United States Patent [19]

Chasalow

[11] Patent Number: 5,830,432
[45] Date of Patent: Nov. 3, 1998

[54] PHOSPHOLIPID DRUG DERIVATIVES

[75] Inventor: Fred I. Chasalow, San Carlos, Calif.

[73] Assignee: Amur Pharmacuticals, Inc., Belmont, Calif.

[21] Appl. No.: 829,078

[22] Filed: Mar. 31, 1997

[51] Int. Cl.⁶ .................................................. A61K 47/44
[52] U.S. Cl. .................... 424/1.77; 514/177; 514/420; 514/422; 514/533
[58] Field of Search .................... 424/1.77; 514/177, 514/772, 420, 422, 533

[56] References Cited

U.S. PATENT DOCUMENTS

| | | | |
|---|---|---|---|
| 4,552,869 | 11/1985 | Lautenschlager et al. | 514/71 |
| 4,721,612 | 1/1988 | Janoff et al. | 424/1.1 |
| 4,780,455 | 10/1988 | Liebermann et al. | 514/77 |
| 4,891,208 | 1/1990 | Janoff et al. | 424/1.1 |
| 4,897,385 | 1/1990 | Wissner et al. | 514/77 |
| 4,916,249 | 4/1990 | Brachwitz et al. | 558/169 |
| 5,194,654 | 3/1993 | Hostetler et al. | 558/152 |
| 5,405,766 | 4/1995 | Kallung et al. | 435/174 |
| 5,411,947 | 5/1995 | Hostetler et al. | 514/43 |
| 5,484,809 | 1/1996 | Hostetler et al. | 514/449 |
| 5,484,833 | 1/1996 | Bombardelli | 424/449 |
| 5,529,989 | 6/1996 | Pettit et al. | 514/81 |
| 5,665,700 | 9/1997 | Cho et al. | 514/2 |
| 5,705,187 | 1/1998 | Ongu | 424/450 |
| 5,709,878 | 1/1998 | Rosenbaum et al. | 424/449 |

FOREIGN PATENT DOCUMENTS 0 135 762  5/1984  European Pat. Off. .

OTHER PUBLICATIONS

Schänzer, Wilhelm, *Clinical Chemistry*, 42(7):1001–1020, 1996.

Cohen, Jon, *Science*, 272:1882–1883, Jun. 28, 1996.

Nugiel, David A. et al., *J. Med. Chem.*, 39:2156–2169, 1996.

*Primary Examiner*—Deborah C. Lambkin
*Attorney, Agent, or Firm*—Darby & Darby

[57] ABSTRACT

Disclosed herein are methods for increasing the aqueous solubility and bio-availability of bioactive agents having a free carboxyl group by conjugating the agent to one or more amino alcohol phosphocholine moieties selected from the group consisting of sphingosylphosphocholine, 2-aminoglycerol phosphocholine, serine-phosphocholine, threonine phosphocholine, tyrosine-phosphocholine, aminoethanol-phosphocholine or hydroxyproline-phosphocholine. Also disclosed herein are pharmaceutical formulations comprising the agents produced by the method.

5 Claims, No Drawings

PHOSPHOLIPID DRUG DERIVATIVES

FIELD OF THE INVENTION

This invention pertains to methods and compositions for increasing the aqueous solubility and bio-availability of bioactive agents by using an amino alcohol moiety as a bridge between a carboxy containing agent and a phospholipid, where the amino alcohol group is selected from the group consisting of sphingosine, 2-aminoglycerol, aminoethanol, serine, threonine, tyrosine, tyramine or similar compounds and the phospholipid is phosphocholine or related compounds.

BACKGROUND OF THE INVENTION

Conventional means for delivering pharmaceutical and therapeutic agents to mammals often are severely limited by chemical and physical barriers to uptake, as well as by susceptibility of administered agents to rapid metabolic inactivation following uptake. Oral delivery of many biologically-active agents would be the route of choice if not for the extreme pH of the stomach, the action of proteolytic and other digestive enzymes in the intestine, and the impermeability of gastrointestinal membranes to the active ingredient.

Methods for orally administering vulnerable pharmacological agents have relied on co-administration of adjuvants (e.g. resorcinols and non-ionic surfactants such as polyoxyethylene oleyl ether and n-hexadecyl polyethylene ether) to artificially increase the permeability of the intestinal walls; co-administration of enzymatic inhibitors (e.g. pancreatic trypsin inhibitor, diisopropylfluorophosphate (DFP) and trasylol) to avoid enzymatic degradation; and encapsulation of the active agent in liposomes or other delivery vehicles.

Irrespective of the mode of administration of many therapeutic compounds, once they gain access to body tissues or fluids they are then subject to rapid inactivation in the liver, termed the "first-pass effect." Orally administered compounds in particular are rapidly delivered to the liver via the portal circulation. Many compounds are acted upon by mixed-function oxidases, Phase I enzymes and other liver enzymes to produce inactive glucuronides, hippurates, glycyl and acetyl derivatives, which are rapidly excreted by the kidney.

There is thus a need in the art for methods and compositions to enable potential therapeutic agents to be rapidly absorbed in the intestine and avoid first-pass inactivation in the liver.

SUMMARY OF THE INVENTION

It has now been unexpectedly discovered that conjugation of many biologically active agents to phospholipids via a phosphodiester bond will significantly enhance the bioactivity and/or the bioavailability of such agents.

In one aspect, the present invention provides a method for increasing the bioavailability of a pharmaceutical agent, comprising the steps of conjugating said agent to one or more amino alcohol moieties selected from the group consisting of sphingosine, 2-aminoglycerol, aminoethanol, serine, threonine, tyrosine, or tyramine producing an intermediate, recovering and coupling the intermediate with phosphocholine or a phosphocholine-like compound to the alcohol group of the intermediate, producing a final conjugate and administering the final conjugate to a mammal wherein the agent in conjugated form is significantly more soluble in aqueous media than the agent in unconjugated form.

In yet another aspect, the present invention provides a composition of matter comprising an isolated phospholipid derivative of Tenidap.

In yet another aspect, the present invention provides a pharmaceutical formulation for treating a mammal suffering from arthritis comprising an isolated phospholipid derivative of a compound selected from the group consisting of Tenidap, indomethacin, salicamide or aspirin and a pharmaceutically acceptable carrier or diluent.

In a still further aspect, the present invention provides a phospholipid derivative of a drug selected from the group consisting of Seratrodast, Isbogrel, Ridogrel, Probenecid and Daltroban.

These and other aspects of the present invention will be apparent to those of ordinary skill in the art in light of the present description, claims and drawings.

DETAILED DESCRIPTION OF THE INVENTION

All patent applications, patents, and literature references cited in this specification are hereby incorporated by reference in their entirety. In case of inconsistencies, the present description, including definitions, will prevail.

Definitions

"Phospholipid-conjugated" or "phospholipid-derivatized" is defined herein as covalently bonded to a phospholipid moiety via a phosphodiester linkage.

"Significantly enhanced bioactivity" or "significantly more soluble in aqueous media" in terms of the conjugated drugs of the present invention is defined herein as no less than 5 to 10-fold increased biological activity and/or aqueous solubility as compared to the unconjugated parent compound when administered by the same route.

"Having a free carboxyl group" is defined herein as a drug with an unconjugated COOH group.

The present invention is directed to increasing the bioavailability and/or aqueous solubility of pharmaceutically active agents, specifically by conjugation of such agents via a free carboxy group to a phospholipid, such as a sphingosylphosphocholine moiety via a phosphodiester bond.

In accordance with the present invention, therapeutic substances will benefit by increasing their water solubility (and their bioavailability) by forming an amide bond between a (a) free amino group, and (b) a phospholipid. Non-limiting examples of the phospholipid include sphingosylphosphocholine, 2-aminoglycerol-phosphocholine, serine-phosphocholine, threonine-phosphocholine, tyrosine-phosphocholine, aminoethanol-phosphocholine, and hydroxyproline-phosphocholine. Sphingosyl-phosphocholine is particularly preferred as the phospholipid because 1) the phosphocholine can be removed by sphingomyelinase which is widely distributed, and 2) the amide linkage can be hydrolysed by the same enzyme that hydrolyses ceramide as part of the sphingosine-ceramide-sphingomyelin cycle.

In accordance with the present invention, conjugation of one or more phospholipid or amino alcohol moieties to lipophilic compounds will render them more hydrophilic, without abrogating their ability to traverse biological membranes. Without wishing to be bound by theory, it is contemplated that phospholipid conjugation will, in most cases, mask the biological activity of the conjugated compounds. The phospholipid conjugates will persist in conjugated form until they encounter enzymes such as phospholipase C, sphingomyelinase and non-specific esterases, which are members of the signal transduction pathway (*Methods in Enzymology*, Vol. 197, E. Dennis, editor, Academic Press, NY) and are present in the circulation and on target tissues. These enzymes will then remove the phospholipid moiety and liberate the original compound with its biological activity intact. The above-mentioned enzymes are specific for phosphocholine; other esterases of the signal transduction system would hydrolyze the other phosphoesters (*Methods in Enzymology*, Vol. 201, T. Hunter, Academic Press, NY, Beth Sefton, editor). In this manner, addition of phospholipid is expected to protect compounds from first-pass inactivation in the liver and allow them to reach their sites of action in the blood or in peripheral tissues.

U.S. patent application Ser. Nos. 08/748,025 and 08/714,864 disclose the use of phospholipid diesters as pro-drugs. The target drug is conjugated via a hydroxyl group to a phospholipid, such as phosphocholine in a phosphodiester linkage. In the present invention, compounds related to sphingomyelin can also be used to produce pro-drugs. That is to say, sphingosine could serve as a bridge between the target drug and the phospholipid. In order to activate the pro-drug, two in vivo enzymatic steps are required: (1) hydrolysis of the phosphodiester bond which serves to release the sphingosine-containing daughter compound, and (2) hydrolysis of N-acyl peptide bond to release the granddaughter target drug. Both of these enzymes are widely distributed and, frequently as part of the signal transduction pathway, are activated in specific tissues by specific activators.

An example of the activation process is provided by the sphingomyelin cycle discussed below.

Sphingomyelin is not a single compound but is actually N-acyl-sphingosyl-phosphoryl choline. The N-acyl groups are long chain fatty acids which can vary from 6 to 24 carbons and have varying degrees of unsaturation. Hydrolysis of the phosphorocholine group by sphingomyelinase produces ceramides (N-acyl-sphingosines). Ceramides oppose the activity of diacylglycerol as a signal transduction factor. In the final step of ceramide action, the N-acyl group is hydrolyzed, leaving free sphingosine and a free long chain fatty acid. The free sphingosine can serve as a substrate for the resynthesis of sphingomyelin (completing the sphingomyelin cycle). The second hydrolytic step eliminates ceramides from the internal cellular fluid and restores the ability of the cells to respond to diacylglyerol as a signal transduction factor.

In addition, 2-aminoglycerol, aminoethanol, tyramine or an amino acid selected from the group consisting of serine, threonine or tyrosine can be used in this alternative embodiment as the conjugating group. In each case, the conjugate could also be cleaved by a peptidase present in normal serum. For use in the present invention, these amino alcohols are converted to phosphocholine derivatives as disclosed in International Application No. PCT/US95/15100.

For use in the present invention, sphingosine, 2-aminoglycerol, tyramine, aminoethanol, serine, threonine and tyrosine can all be obtained from Sigma (St. Louis, Mo.). As mentioned above, in this embodiment of the invention, the target drugs have a carboxy group as the site of linkage to the phospholipid. The synthesis of the new compounds would be by dicyclohexylcarbodiimide- or a water soluble carbodiamide-catalyzed (commercially available from Pierce, Rockford, Ill.) formation of a peptide bond between the carboxy-containing target drugs and the amino group of sphingosine, 2-aminoglycerol or the amino acids serine, threonine or tyrosine. The carboxy group of the amino acid would be protected. The peptide could then be esterified with phosphorus oxychloride and connected to a phosphocholine diester or an analog with the procedures already described. In vivo, the sphingosine or aminoalcohol is cleaved by a peptidase to release the target drug. This reaction is shown below.

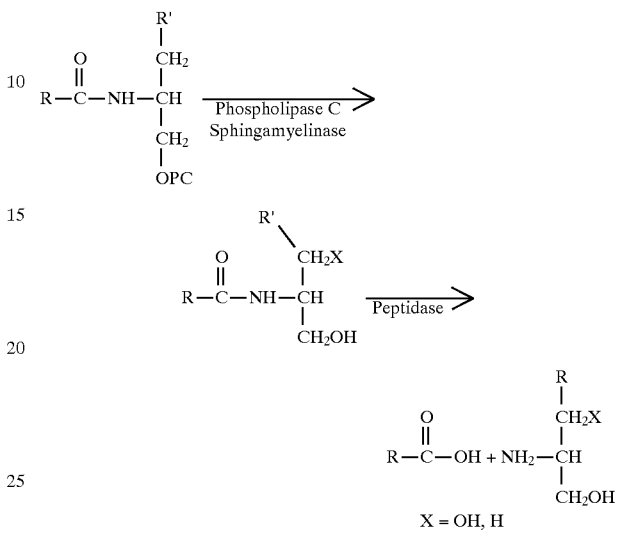

Presented below is a non-limited list of target drugs for use in the present invention. Following the name of the compound, presented in parenthesis is the number assigned to the compound in the Merck Index, 1996, 12th edition. Seratrodast (8603), Isbogrel (5120), Indomethacin (4998), Ridogrel (8379), Aspirin (886), Probenecid (7934), Tenidap (9290), Daltroban (2871). All of these compounds, with the exception of Aspirin, would be expected to be more soluble in aqueous media and hence more bioavailable when administered to mammals. Phospholipid conjugation of Aspirin is expected to produce a long acting derivative of the drug, i.e. it will persist in the circulation until cleaved (activated) by serum esterases.

In addition to phosphocholine, other choline derivatives can be employed to produce the conjugates of the present invention. These include homo-choline, methylcholine, N,N-dimethylcholine, N-R, aminoethanolcholine, wherein R=alkyl or aryl. The synthesis of these choline analogs is shown in Example 4 below whereas Example 5 shows the synthesis of DHEA-3-homo-choline.

Particularly preferred for use in the present invention are Tenidap and related anti-inflammatory and analgesic compounds disclosed in U.S. Pat. No. 4,569,942. These compounds, along with Aspirin and Indomethacin, can be conjugated to phospholipids and/or phosphocholine-amino alcohols pursuant to the present invention and used to treat, e.g. arthritis. It is expected that these conjugated agents will be more effective due to their increased aqueous solubility.

Presented below in Example 1 is an example of the synthesis of a phospholipid drug derivative produced pursuant to the present invention.

Presented below in Example 2, are the structures of sphingosine, sphingosylphosphorylcholine, sphingomyelin, and an example of a pro-drug manufactured according to the present invention. Presented below in Example 3 is an example of a preferred pro-drug, Tenidap, conjugated pursuant to the present invention.

The derivatized drugs of the present invention can be incorporated into pharmaceutical formulations to be used to treat mammals. Pharmaceutical formulations comprising the phospholipid-conjugated drugs of the present invention as at least one of the active ingredients, would in addition optionally comprise pharmaceutically-acceptable carriers, diluents, fillers, salts and other materials well-known in the art depending upon the dosage form utilized. For example, preferred parenteral dosage forms may comprise a sterile isotonic saline solution, 0.5 N sodium chloride, 5% dextrose and the like. Methyl cellulose or carboxymethyl cellulose may be employed in oral dosage forms as suspending agents in buffered saline or in cyclodextran solutions to enhance solubility.

It will be appreciated that the unit content of active ingredient or ingredients contained in an individual dose or dosage form need not in itself constitute an effective amount for the various usages of the phospholipid-derivatized drugs of the present invention since the necessary effective amount can be reached by administration of a plurality of such dosage forms.

The following examples are intended to further illustrate the present invention without limiting it thereof.

Sphingosine

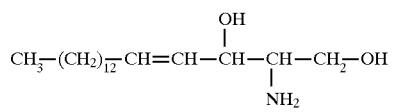

Sphingosylphosphorycholine

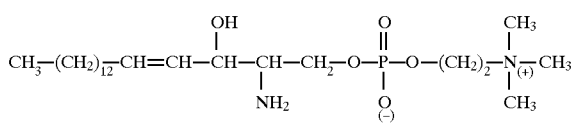

Sphingomyelin

Synthesis of Phospholipid Drug Derivative

Aspirin

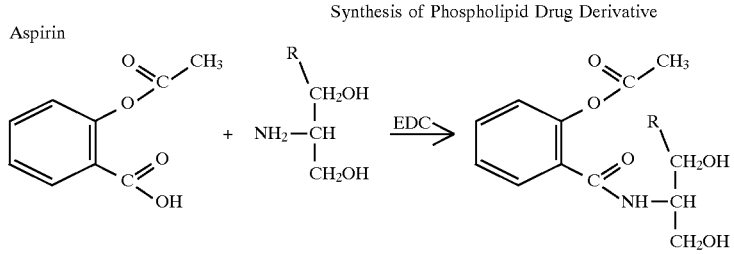

EDC = water soluble carbodiimide available from Pierce available from Aldrich

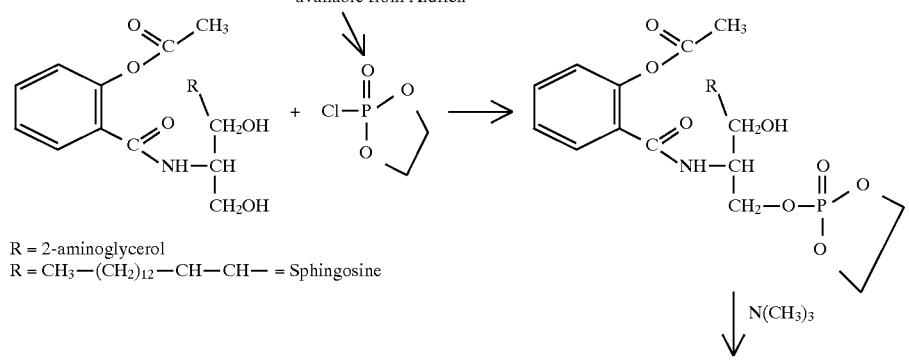

R = 2-aminoglycerol
R = CH$_3$—(CH$_2$)$_{12}$—CH—CH— = Sphingosine (must use stoichiometric amounts of to prevent reaction with second hydroxy group)

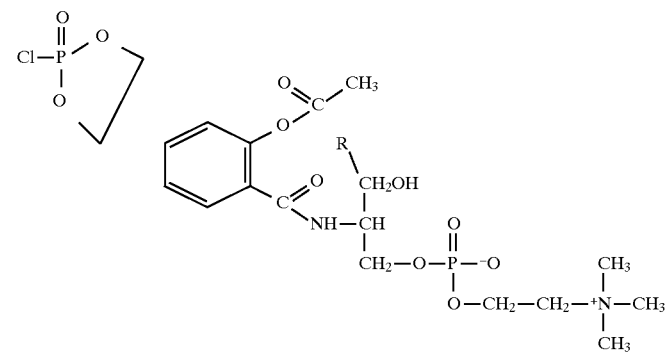

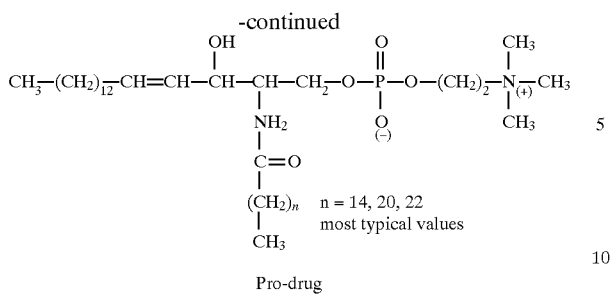
Pro-drug
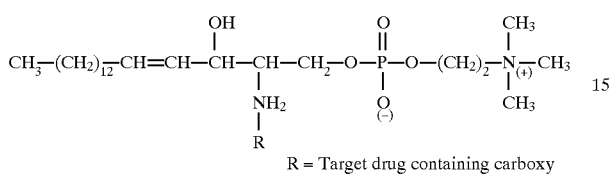
R = Target drug containing carboxy
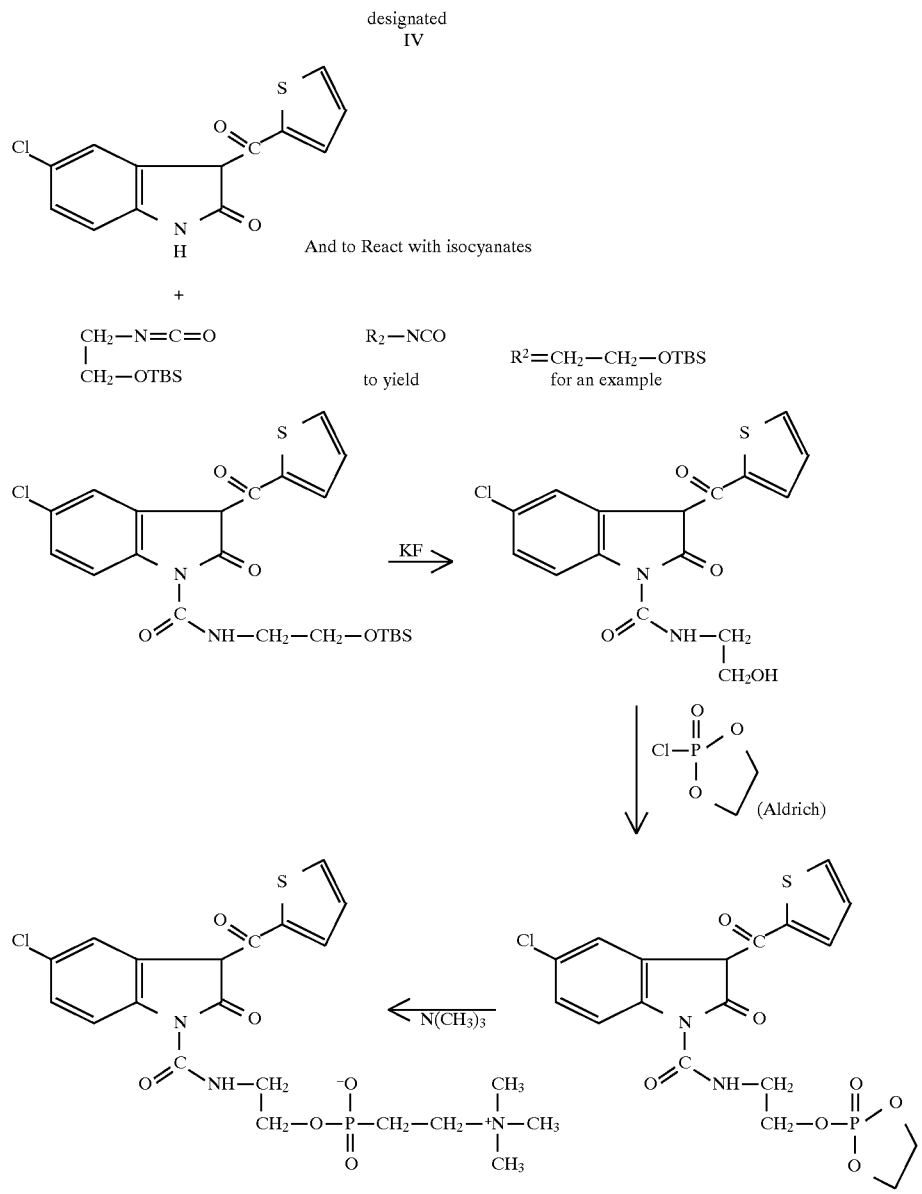

R—OH  where R = alcohol-containing amino acid or
       another alcohol-containing compound
Examples of R—OH
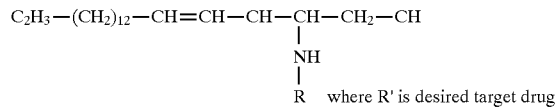
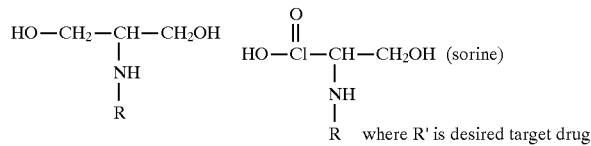
Chemistry example for DHEA as R—OH
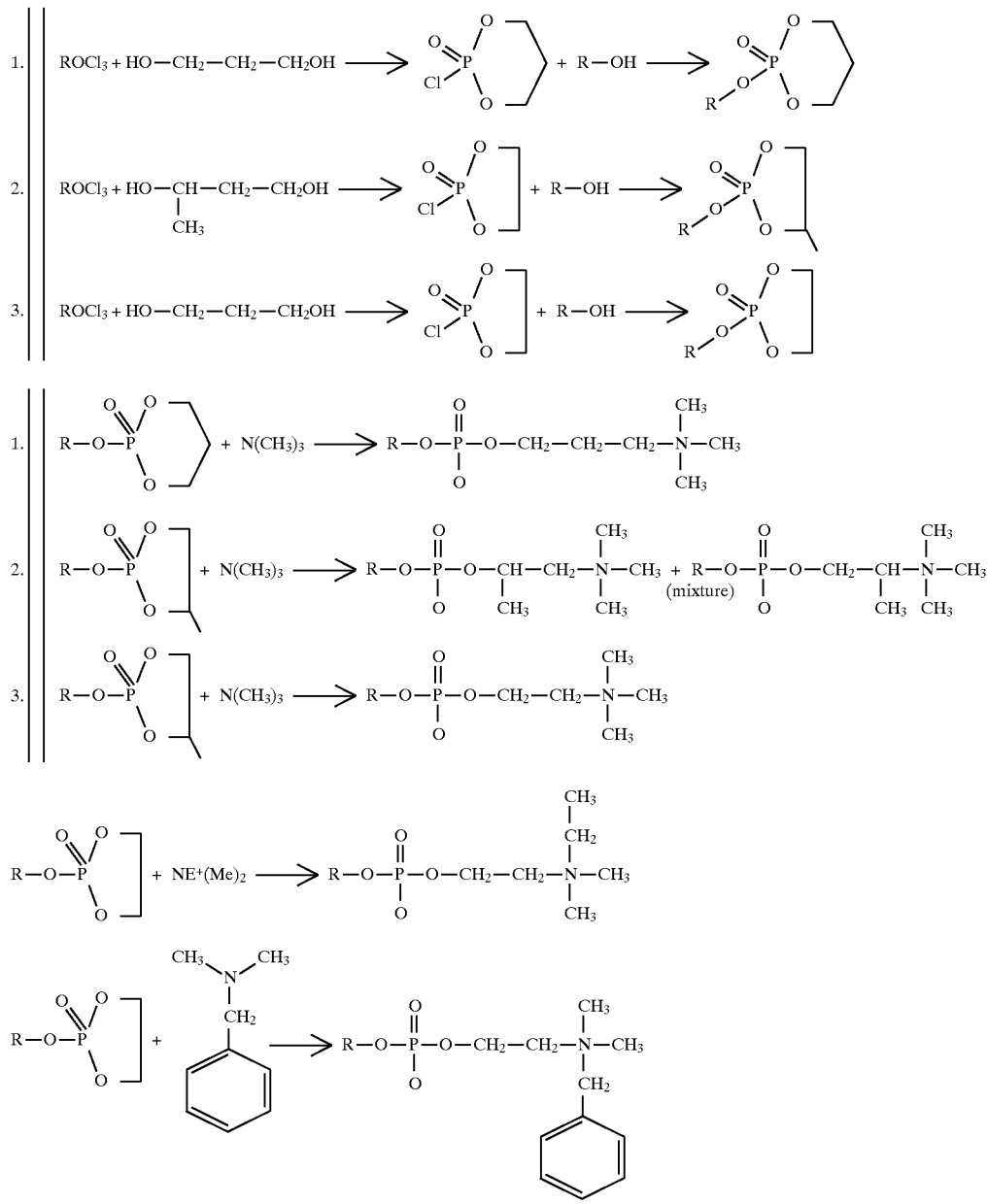

-continued

The amino acids have to be protected with a t-butyl ester and then the tbutyl group must be released by mild base catalysis. The latter step would be catalysed by the base used to open the ring, for example, $N-(CH_3)_3$ or $N-(CH_2)_2-CH_2-CH_3$ This pathway leads to homo-choline and methylcholine Note that path -2 leads to chiral compounds R—OH (R = DHEA as an example)

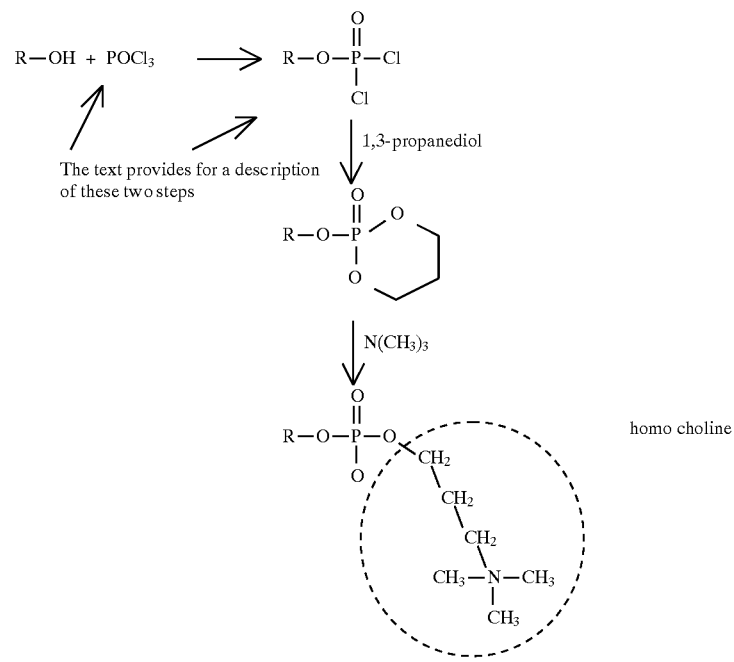

homo choline

EXAMPLE 5: SYNTHESIS OF DHEA-3-HOMOPHOSPHOCHOLINE

DHEA (5.76 g, 20 mmol) Triethylamine (Fisher) (3.4 ml, 2.5 g, 25 mmol) were dissolved in dry benzene (300 ml) in a 500 ml round bottomed (Ciba) flask. Phosphorus oxychloride (Aldrich) (2.1 ml, 3.5 g, 23 mmol) was added at room temperature (r.t.) The reaction mixture was magnetically stirred at r.t. and the progress of the reaction was monitored with thin layer chromatography (TLC). After four hours, the DHEA was completely converted into the intermediate product. The precipitated salt was filtered off by passing through a sintered addition funnel under nitrogen pressure with the aid of a canula into another 500 ml, 2-neck, round bottomed flask. The salt was washed once with a small amount of dry benzene. The addition funnel was removed and the flask was connected to a nitrogen inlet tube. 1,3-propanediol (1.8 ml, 1.9 g, 25 mmol) (Fisher) was added in one portion while the solution was rapidly stirred following the addition. Triethylamine (6.9 ml, 5 g, 50 mmol) was added and the mixture was stirred at r.t. and was monitored with TLC. When the conversion was complete, the salt was filtered using a Buchner funnel and washed with regular benzene. The solvent was removed on a rotary evaporator and the residue was vacumm dried for 8 hours. Following the procedure for making DHEA-3-phosphocholine, formation of DHEA-3-phosphohomocholine was materialized.

What is claimed is:

1. A method for increasing the aqueous solubility of a pharmaceutical agent, said agent having a free carboxyl group comprising the steps of conjugating said agent to one or more amino alcohol phosphocholine moieties selected from the group consisting of sphingosylphosphocholine, 2-aminoglycerol-phosphocholine, serine-phosphocholine, threonine-phosphocholine, tyrosine-phosphocholine, aminoethanol-phosphocholine, or hydroxyproline-phosphocholine forming a diester with said alcohol, and recovering said biologically active agent conjugated to said amino alcohol phosphocholine moieties.

2. A pharmaceutical formulation for treating a mammal suffering from arthritis comprising a phospholipid-conjugated compound selected from the group consisting of Tenidap, aspirin or indomethacin and a pharmaceutically-acceptable carrier or diluent, wherein said phospholipid is selected from the group consisting of sphingosylphosphocholine, 2-aminoglycerol-phosphocholine, serine-phosphocholine, threonine-phosphocholine, tyrosine-phosphocholine, aminoethanol-phosphocholine, or hydroxyproline-phosphocholine.

3. A Phospholipid derivative of a drug selected from the group consisting of Seratrodast, Isbogrel, Ridogrel, Probenecid or Daltroban and a pharmaceutically-acceptable carrier or diluent, wherein said phospholipid is selected from the group consisting of sphingosylphosphocholine, 2-aminoglycerol-phosphocholine, serine-phosphocholine, threonine-phosphocholine, tyrosine-phosphocholine, aminoethanol-phosphocholine, or hydroxyproline-phosphocholine.

4. The method of claim 1 wherein the diester is with a choline analog selected from the group consisting of methyl choline, homocholine, N,N-diethylcholine, or N-R amino ethanolcholine, wherein R is H, alkly or Aryl.

5. A composition of matter comprising DHEA-3-homophosphocholine.

* * * * *